(12) United States Patent
Zhao et al.

(10) Patent No.: US 8,546,620 B2
(45) Date of Patent: Oct. 1, 2013

(54) ETHYLENE GLYCOL REMOVAL OF RESIDUAL GLYCOL IMPURITIES

(75) Inventors: Haibo Zhao, The Woodlands, TX (US); Matthew W. Forkner, Spring, TX (US); Wenjin Zhang, Fort Erie, CA (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 788 days.

(21) Appl. No.: 12/531,895

(22) PCT Filed: Mar. 14, 2008

(86) PCT No.: PCT/US2008/056990
§ 371 (c)(1),
(2), (4) Date: Sep. 18, 2009

(87) PCT Pub. No.: WO2008/115787
PCT Pub. Date: Sep. 25, 2008

(65) Prior Publication Data
US 2010/0105966 A1    Apr. 29, 2010

(51) Int. Cl.
*C07C 29/76* (2006.01)

(52) U.S. Cl.
USPC .......................... 568/872; 568/917

(58) Field of Classification Search
USPC ................... 568/872, 917
See application file for complete search history.

(56) References Cited

U.S. PATENT DOCUMENTS

| | | | |
|---|---|---|---|
| 2,908,639 A | 10/1959 | Carter et al. | |
| 4,588,847 A | 5/1986 | Chou | |
| 5,425,853 A | 6/1995 | Berg | |
| 6,034,281 A | 3/2000 | Egedy et al. | |

OTHER PUBLICATIONS

Aldrich Catalog Handbook of Fine Chemicals, 1992-1993, Product No. 24,122-9.*

* cited by examiner

*Primary Examiner* — Elvis O Price
(74) *Attorney, Agent, or Firm* — Huntsman International LLC

(57) ABSTRACT

A process includes receiving a process stream including at least about 80.0% by weight propylene glycol, and contacting the process stream with an absorbent material to produce a product stream. The absorbent material is configured to preferentially absorb ethylene glycol relative to propylene glycol.

22 Claims, 5 Drawing Sheets

ETHYLENE GLYCOL REMOVAL OF RESIDUAL GLYCOL IMPURITIES

CROSS-REFERENCE TO RELATED APPLICATIONS

This application is the National Phase of International Application PCT/US2008/056990 filed Mar. 14, 2008 which designated the U.S. and which claims priority to U.S. Provisional App. Ser. No. 60/896,197 filed Mar. 21, 2007. The noted applications are incorporated herein by reference.

FIELD OF THE DISCLOSURE

This disclosure, in general, relates to removal of residual glycol impurities from a propylene glycol stream.

BACKGROUND

Production of propylene glycol (PG) from glycerin is becoming increasingly attractive relative to traditional hydration of propylene oxide due to the availability of inexpensive glycerin. On the other hand, traditional methods for producing PG from propylene oxide do not produce toxic byproducts, such as ethylene glycol (EG). In contrast, the process for producing PG from glycerin uses a heterogeneous catalyst, which also forms EG.

Particular grades of PG are used in foods and medicine. On the other hand, EG is toxic and harmful to mammals. Traditionally, distillation is used to separate PG and EG. However, due to the similar chemical natures of EG and PG, reduction of EG content to low levels is extremely expensive via conventional distillation. A very large number of stages and very high reflux ratios are used, resulting in high capital and operating costs.

As such, improved techniques for removing EG impurities from PG would be desirable.

SUMMARY

In a particular embodiment, a process includes receiving a process stream including at least about 80.0% by weight propylene glycol, and contacting the process stream with an absorbent material to produce a product stream. The absorbent material is configured to preferentially absorb ethylene glycol relative to propylene glycol.

In another exemplary embodiment, a process for producing high purity propylene glycol includes receiving a process stream including at least about 80.0% by weight propylene glycol and including ethylene glycol in an amount of less than about 5.0% by weight, and contacting the process stream with a zeolite material to produce a product stream. The zeolite material is configured to preferentially absorb the ethylene glycol relative to propylene glycol.

In a further exemplary embodiment, a process for producing high purity propylene glycol includes receiving a stream including at least about 60.0% by weight propylene glycol and including ethylene glycol, distilling the stream to produce a process stream including at least about 80.0% by weight propylene glycol and not greater than 5.0% by weight ethylene glycol, and contacting the process stream with an absorbent material configured to preferentially absorb the ethylene glycol relative to the propylene glycol.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DESCRIPTION OF THE PREFERRED EMBODIMENT(S)

In a particular embodiment, a process for producing high purity propylene glycol includes receiving a process stream including at least about 80.0% by weight propylene glycol and contacting the process stream with an absorbent material to produce a product stream. The process stream may include ethylene glycol impurities in amounts not greater than about 5.0% by weight. The resulting product stream may include not greater than 2000 ppm ethylene glycol and preferably not greater than 50 ppm ethylene glycol.

The process also may include a distillation column configured to partially remove impurities. For example, the distillation column may receive a stream that includes at least about 60.0% by weight propylene glycol and produce a process stream that includes at least about 80.0% by weight propylene glycol. The process steam may be contacted with the absorbent material.

Figure 1:
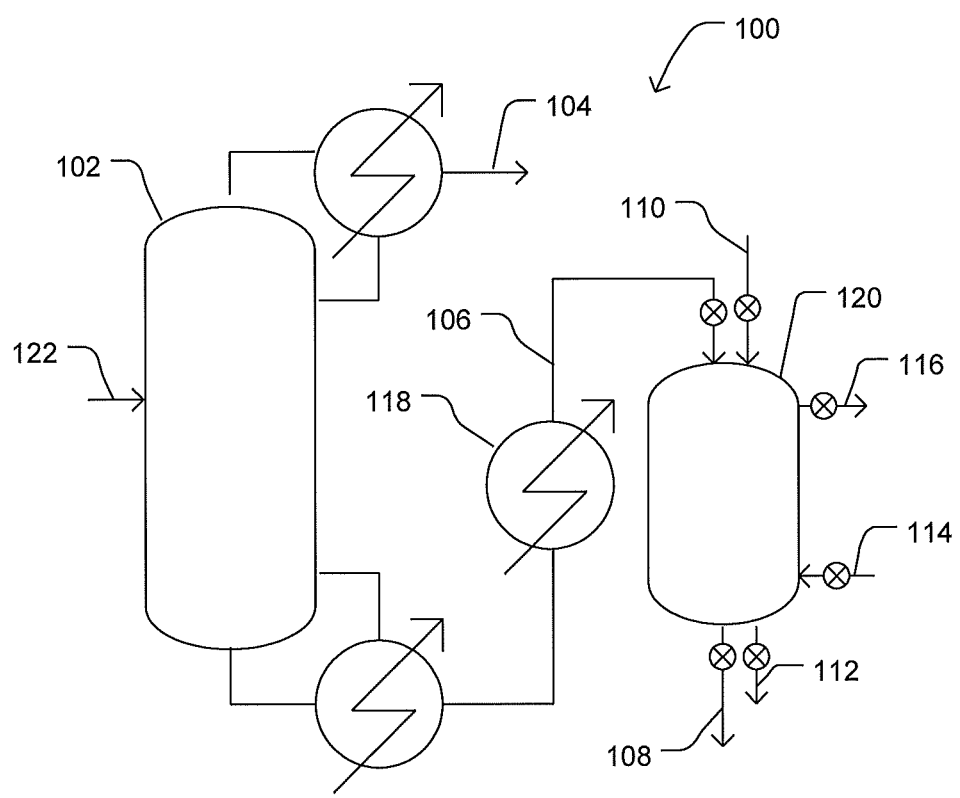
FIG. 1 includes an illustration of an exemplary process flow.

FIG. 1 includes an illustration of an exemplary process for treating propylene glycol streams. In the illustrated embodiment, a process stream 106 including propylene glycol is fed to at least one contacting vessel 120 that includes an absorbent material. In an exemplary embodiment, the process stream 106 may be pretreated using other separation technologies, such as a distillation column 102. Further, the process stream 106 optionally may be preconditioned, such as temperature conditioning using a heat exchanger 118, prior to contacting with the absorbent material.

In the illustrated embodiment, a feed stream 122 includes at least about 60% by weight propylene glycol and may include other impurities, such as ethylene glycol or lactic acid. In particular, the feed stream 122 may include at least about 225 ppm ethylene glycol. In another embodiment, feed stream 122 may include at least about 500 ppm ethylene glycol. In yet another embodiment, feed stream may include at least about 1000 ppm ethylene glycol, preferably at least about 2000 ppm ethylene glycol. In another embodiment, feed stream 122 may include 1.5% by weight ethylene glycol or even as high as about 5.0% by weight or higher ethylene glycol. As illustrated, the feed stream 122 may be fed to a distillation column 102, which may separate some of the impurities. For example, an effluent stream 104 may include a portion of the impurities and may include some propylene glycol. Alternatively, the feed stream 122 may be fed directly to the contacting vessel 120.

In a particular embodiment, the distillation column 102 produces a process stream 106 that includes at least about 80.0% by weight propylene glycol. For example, the process steam 106 may include at least about 85.0% by weight propylene glycol, such as at least about 95.0% by weight propylene glycol, or even at least about 99.0% by weight propylene glycol. In addition, the process steam 106 may include impurities, such as ethylene glycol. For example, the process steam 106 may include at least about 225 ppm ethylene glycol, such as at least about 500 ppm ethylene glycol, or at least about 1000 ppm ethylene glycol or even at least about 2000 ppm ethylene glycol. Typically, the process stream 106 includes ethylene glycol in amounts not greater than about 5.0% by weight, or alternatively in amounts not greater than 1.5% by weight. In a particular example, the process stream 106 includes ethylene glycol in a range of about 225 ppm to about 2000 ppm, such as a range of about 500 ppm to about 2000 ppm ethylene glycol, or a range of about 500 ppm to about 1000 ppm ethylene glycol.

In an exemplary embodiment, the process stream 106 may be conditioned, such as through controlling temperature or pressure of the process stream 106. For example, the temperature of the process stream 106 may be conditioned using a heat exchanger 118. Depending at least in part on the temperature of the process stream 106 when it exits distillation column 102, the heat exchanger 118 may be used to heat or cool the process stream 106. In particular, the process stream 106 may be conditioned to a temperature in a range of about 50° C. to about 300° C., such as a range between about 80° C. and about 225° C., or even a range of about 130° C. to about 170° C. The pressure of the process stream 106 may be controlled through pressure drop valves, pumps, or other pressure control mechanisms. For example, the pressure may be adjusted to a range between about 1 psi to about 2000 psi, such as about 15 psi to about 1000 psi, or about 15 psi to about 200 psi. In particular, the pressure may be adjusted to a range of about 50 psi to about 150 psi.

As illustrated, the process stream 106 is fed to a contacting vessel 120. The contacting vessel 120 includes an absorbent material configured to preferentially absorb ethylene glycol relative to propylene glycol. For example, the absorbent material may be an exchange resin or a molecular sieve. In a particular example, the absorbent is a porous material having pore size configured to preferentially separate ethylene glycol from propylene glycol, such as a molecular sieve. An exemplary molecular sieve may include an aluminosilicate material, such as a clay, a zeolite, or any combination thereof. In particular, the absorbent material may be a zeolite, such as an A zeolite, an X zeolite, a Y zeolite, or any combination thereof. In particular, the absorbent material is an A zeolite in sodium form, such as a 4 A zeolite, a 3 A zeolite, a 5 A zeolite, or any combination thereof. Preferably, the absorbent material is a 4 A zeolite.

Optionally, the contacting vessel 120 may be heated to maintain a temperature in a range of about 50° C. to about 300° C., such as a temperature in a range between about 80° C. and about 200° C., preferably between about 140° C. and about 160° C. and more preferably between about 145° C. and about 155° C.

While the system 100 illustrated in FIG. 1 is illustrated to include a single contacting vessel 120. The system 100 may include at least one contacting vessel, such at least two contacting vessels. The contacting vessels may be placed in service at different times or undergo different processing at different times, such as contacting with the process stream 106, washing the absorbent material, or drying. In particular at least one contacting vessel may be in service in contact with the process stream 106 while another contacting vessel is being regenerated, for example, washing and drying.

In the illustrated example, the contacting vessel 120 is a fixed bed contacting vessel. Alternatively, the contacting vessel 120 may be a fluidized bed or may utilize other methods for facilitating contact between the absorbent material and the process stream 106. Further, the contacting vessel 120 is illustrated in a down flow configuration. Alternatively, the contacting vessel 120 may be configured in an up flow configuration.

As the process stream 106 is contacted with the absorbent material of the contacting vessel 120, ethylene glycol is preferentially absorbed relative to propylene glycol. As such, the product stream 108 generally has a reduced level of ethylene glycol. For example, the product stream 108 may include not greater than about 300 ppm ethylene glycol, such as not greater than about 100 ppm ethylene glycol, or not greater than about 50 ppm ethylene glycol, or even not greater than about 25 ppm ethylene glycol. In addition, the product stream 108 may include at least about 95.0% by weight propylene glycol, such as at least about 98.0% by weight propylene glycol, at least about 99.0% by weight propylene glycol, at least about 99.5% by weight propylene glycol, or even at least about 99.8% by weight or higher propylene glycol.

The system 100 illustrated in FIG. 1 may include valves and other flow controlling devices to isolate the absorbent material bed or contacting vessel 120 from the process stream 106. In particular, the contacting vessel 120 may be isolated from the process stream 106 in order to regenerate the absorbent material. For example, the absorbent material may be regenerated by supplying a polar solvent through solvent stream 110 to the contacting vessel 120. The polar solvent and any desorbed material may exit through waste stream 112.

After extraction of the absorbed components, the absorbent material may be further treated such as, for example, drying. An inert drying gas, such as air or $N_2$, may be fed into the contacting vessel through stream 114 and may exit through stream 116. Optionally, the inert drying gas may be heated.

While the illustrated system 100 includes a distillation column 102, an alternative embodiment of the system may not include a distillation column 102. Instead, the sizing or number of contacting vessels 120 may be altered to compensate for the additional impurities experienced by directly feeding feed stream 122 into the contacting vessel 120. Distillation column 102 may be effective at removing some impurities to a particular level. However, achieving low concentrations of impurities that have similar vapor pressures to the desired product uses a larger column, a higher reflux or more energy and is often cost prohibitive.

While the exemplary embodiment illustrated in FIG. 1 includes a set of streams and valves, other embodiments and arrangements of equipment may be envisaged to effect the described process. For example, different conduit and valve configurations may be envisaged to permit sequential access to the contacting vessel or vessels 120 to facilitate contacting, washing, and drying. In other examples, vessel configuration may permit sections of the vessel to simultaneously undergo different parts of the process. In a further example, the process may operate in batch mode. For example, a propylene glycol effluent may be contacted with the absorbent material in batch mode and the resulting propylene glycol product can be decanted or filtered from the mixture once a desired purity is acquired.

Figure 2:
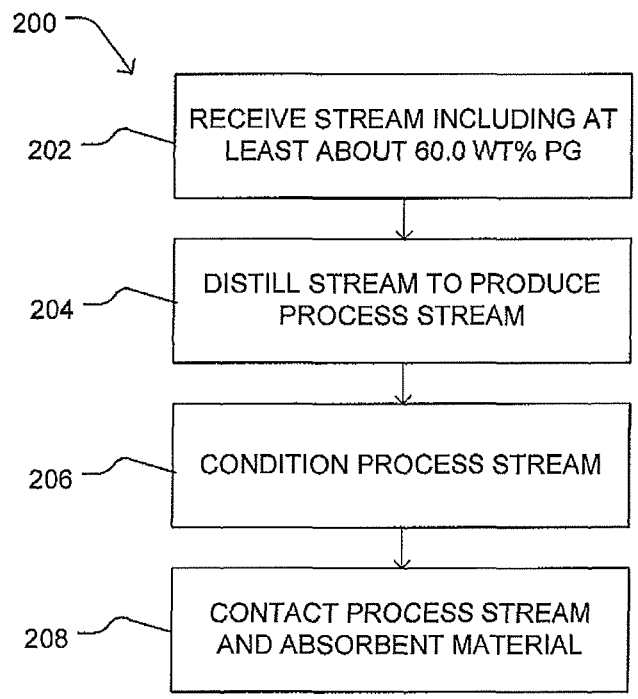
FIG. 2 and FIG. 3 include flow diagrams illustrating exemplary processes.

FIG. 2 includes an illustration of an exemplary method 200 for treating a propylene glycol process stream. For example, the system may receive a stream including at least about 60.0% by weight propylene glycol, as illustrated at 202. The stream may also include other impurities, such as lactic acid and ethylene glycol. For example, the stream may include at least about 225 ppm ethylene glycol, such as at least about 500 ppm ethylene glycol, at least about 1000 ppm ethylene glycol, at least about 2000 ppm ethylene glycol, or even as high as 5.0% by weight or higher ethylene glycol.

Optionally, the feed stream may be fed into a distillation column, as illustrated at 204. For example, the distillation column may produce a process stream that includes at least about 80.0% by weight propylene glycol. The process stream, for example, may include at least about 80.0% by weight propylene glycol and may include ethylene glycol in amounts between about 225 ppm ethylene glycol and 2000 ppm ethylene glycol, such as a range between about 500 ppm to about 2000 ppm ethylene glycol, or the process stream may include ethylene glycol in amounts as high as 5% by weight.

Further, the process stream may be conditioned, for example, to control temperature and pressure, as illustrated at 206. For example, a heat exchanger may be used to adjust the temperature of the process stream to a temperature range of about 50° C. to about 300° C., such as a temperature in a range between about 80° C. and about 225° C. or even a range of about 130° C. to about 170° C. The pressure may be adjusted to a range between about 1 psi to about 2000 psi, such as about 15 psi to about 1000 psi, or about 15 psi to about 200 psi. In particular, the pressure may be adjusted to a range of about 50 psi to about 150 psi.

In a particular embodiment, the process stream is contacted with an absorbent material, as illustrated at 208. The absorbent material preferentially absorbs ethylene glycol relative to propylene glycol. As a result, a product stream is produced that includes not greater than about 2000 ppm ethylene glycol, such as not greater than about 500 ppm ethylene glycol, or not greater than about 300 ppm ethylene glycol, or not greater than about 100 ppm ethylene glycol, or not greater than about 50 ppm ethylene glycol, or even not greater than about 25 ppm ethylene glycol. In addition, the product stream may include at least about 95.0% by weight propylene glycol, such as about 98.0% by weight propylene glycol, at least about 99.0% by weight propylene glycol, or even at least about 99.8% by weight propylene glycol.

Figure 3:
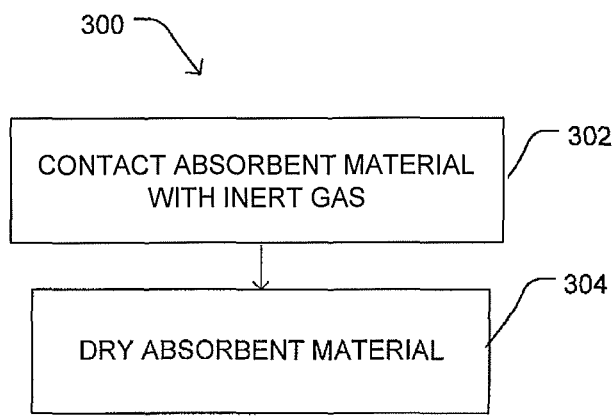

In a particular embodiment, the absorbent material may be regenerated once it has reached its capacity for absorbing the impurities of the process stream. As illustrated in an exemplary method 300 in FIG. 3, the absorbent material may be contacted with an inert gas, as illustrated at 302, to remove residual.

To further facilitate regeneration, the absorbent material may be dried, as illustrated at 304. For example, an inert gas may be introduced and the absorbent material may be maintained at a regeneration temperature of about 150° C. to about 800° C. for a period of time, such as up to about 24 hours. The absorbent material may then be cooled.

In another embodiment, the absorbent material may be regenerated in the same or different contacting vessel, or the absorbent material may be removed from the contacting vessel and regenerated in a drying oven.

Once the absorbent material is regenerated, it may be placed back into service and contacted with the propylene glycol process stream.

Thus, in one embodiment, regeneration is carried out by first supplying an inert gas, for example, air, oxygen or nitrogen or any mixture thereof, to the contacting vessel to purge any residual liquid remaining in the contacting vessel. A vacuum may also be applied to the contacting vessel, either as an additional step or as an alternative to the nitrogen purge, to remove (or further remove) any residual liquid from the absorbent material and contacting vessel. Such residual liquid may then be collected and combined with the propylene glycol process stream for treatment. The contacting vessel may then be heated to a temperature of about 300° C. and air, heated to a temperature of about 300° C., may then be introduced into the contacting vessel at a suitable flow rate. The contacting vessel may then be maintained at a regeneration temperature of about 150° to about 800° C. for a period of time within the range of between about 0.5 to about 24 hours. Cool air may then be supplied to the contacting vessel, at a suitable flow rate to cool the absorbent material. An inert gas, for example nitrogen gas, may also be introduced into the contacting vessel to further cool the absorbent material to a temperature of about 150° C. The regenerated dried absorbent material may then be contacted with the propylene glycol process stream.

Particular embodiments of the process provide technical advantages not found in the prior art. In particular, the process produces a greater purity propylene glycol product with less energy and equipment cost. Many glycerol to propylene glycol processes co-produce ethylene glycol, which is a known harmful molecule to mammals. The ethylene glycol impurity greatly limits the usage of propylene glycol in many fields. Although ethylene glycol may be removed by distillation, the cost of distillation to remove ethylene glycol from concentrations greater than 500 ppm ethylene glycol to concentrations below 50 ppm ethylene glycol is high. In particular embodiments of the absorption process, zeolite selectively adsorbs ethylene glycol relative to propylene glycol, resulting in ethylene glycol concentrations below 50 ppm. The zeolite is easily regenerated by optionally washing with polar solvents and drying. As a result, the cost to reduce ethylene glycol concentrations by the present process is low relative to distillation processes.

EXAMPLES

Example 1

Crude propylene glycol with 1.5% by weight ethylene glycol contamination was pumped to a heat exchanger and conditioned to a temperature of about 150° C. The conditioned crude propylene glycol was introduced at a flow rate of 125 g/h into a 4 A zeolite bed having a bed temperature of 150°. The bed was constructed with stainless steel and had an OD of 0.75 inches and length of 3 feet. The propylene glycol effluent stream was collected over a 2.5 hour time period and exhibited a reduced level of ethylene glycol matching to 301 ppm ethylene glycol.

The 4 A zeolite bed was then regenerated by purging the system with nitrogen gas followed by the introduction of 300° C. air at a flow rate of 14 SCFH. The temperature of the bed was maintained within the range of 500° C. to 700° C. for 30 minutes. The bed was then cooled to a temperature of about 200° C. by cool air (flow rate of 14 SCFH) and then further cooled by nitrogen gas to a temperature of about 150° C. The regenerated bed was subjected to crude propylene glycol with 1.5% by weight ethylene glycol contamination as above and functioned similarly in terms of reducing ethylene glycol contamination in the propylene glycol effluent.

Example 2

Figure 4:
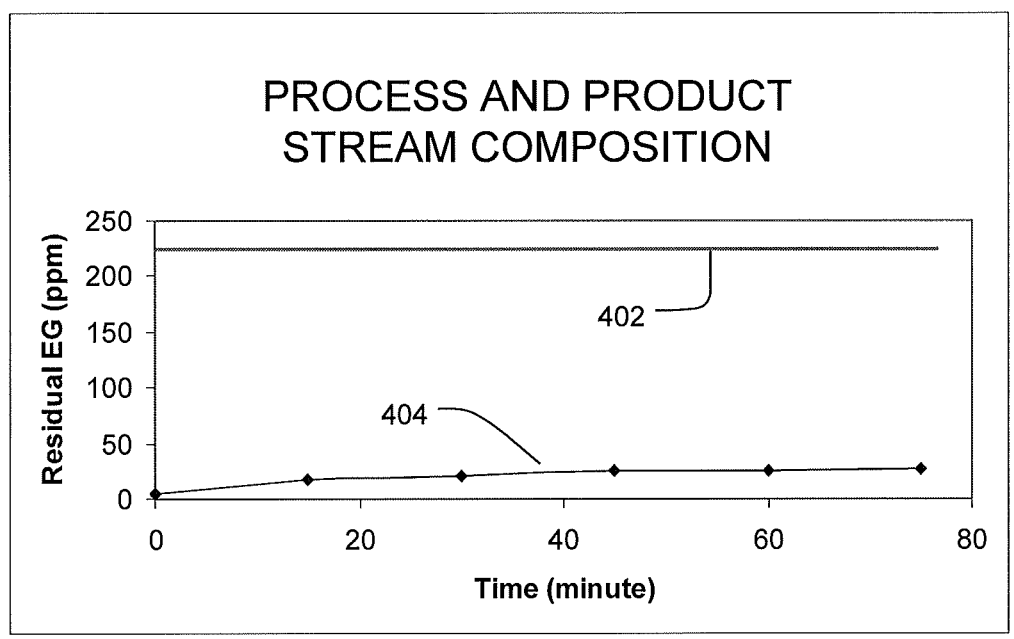
FIG. 4 includes an illustrative graph of product stream composition.

Crude propylene glycol with 225 ppm ethylene glycol contamination was pumped and preheated to 100° C. in a pre-heating column. The pre-heated crude propylene glycol was introduced into a 4 A zeolite bed with bed temperature of 100° C. The bed was constructed with stainless steel and had an OD of 0.5 inches and length of 11 feet. A backpressure regulator was set to provide a pressure of 100 psi. The flow rate was determined to be 100 g/h by measuring the reduction in weight in the feed vessel. The propylene glycol effluent was collected and analyzed by gas chromatography. FIG. 4 illustrates that the concentration of ethylene glycol in the feed stream 402 was greater than 200 ppm and was reduced to an ethylene glycol concentration in the propylene glycol effluent stream 404 of about 25 ppm ethylene glycol.

Example 3

Figure 5:
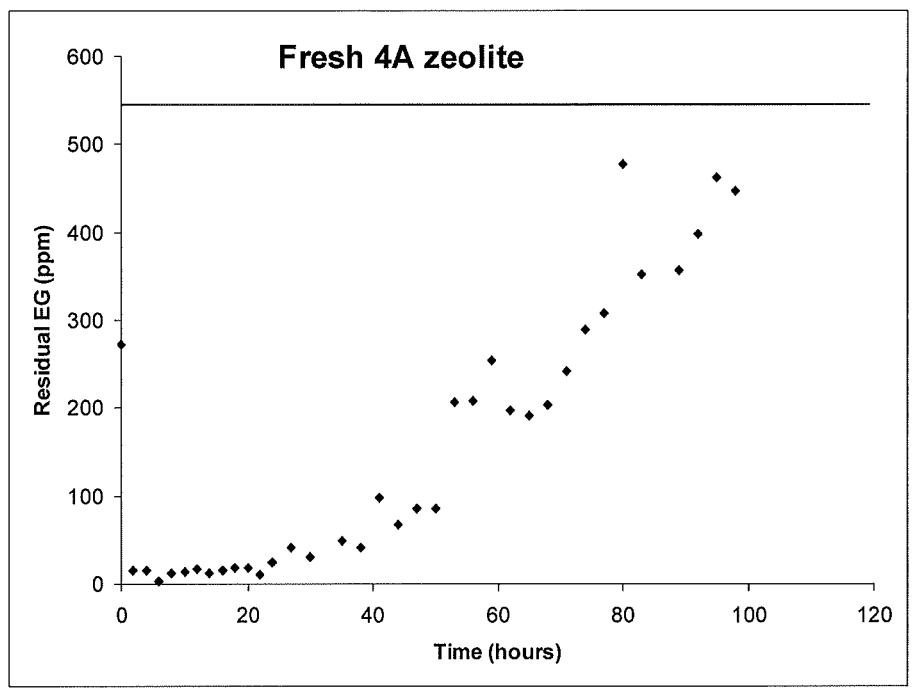
FIG. 5 and FIG. 6 include illustrative graphs of product stream composition produced from fresh and regenerated absorbent material.

Crude propylene glycol with 544 ppm ethylene glycol contamination was pumped and preheated to 100° C. in a pre-heating column. The pre-heated crude propylene glycol was introduced into a 4 A zeolite bed with bed temperature of 100° C. The bed was constructed with stainless steel and had an OD of 0.5 inches and length of 6 feet. A backpressure regulator was set to provide a pressure of 100 psi. The flow rate was determined to be 100 g/h by measuring the reduction in weight in the feed vessel. The propylene glycol effluent was collected and analyzed by gas chromatography. FIG. 5 illustrates that the concentration of ethylene glycol in the feed stream was reduced from 544 ppm ethylene glycol to less then 20 ppm ethylene glycol for a period of about 24 hours.

Figure 6:
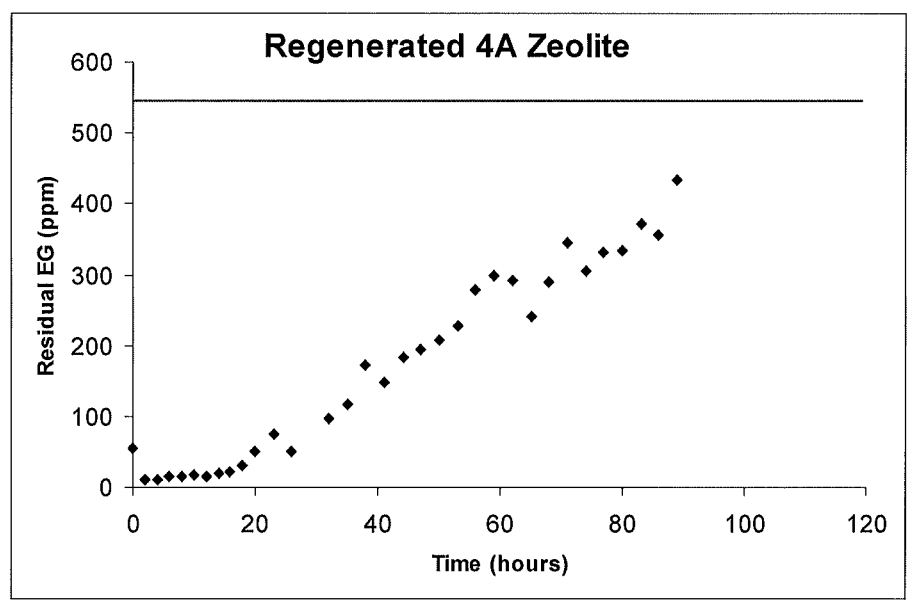

The 4 A zeolite bed was then regenerated by exposing the bed to air at 80 SCFH followed by heating at 500° C. for 24 hours and subsequent cooling. Crude propylene glycol with 542 ppm ethylene glycol contamination was then introduced into the 4 A zeolite bed as above and the propylene glycol effluent stream collected and analyzed. FIG. 6. illustrates that the concentration of ethylene glycol in the feed stream was reduced by the regenerated zeolite bed from 542 ppm ethylene glycol to less than 20 ppm ethylene glycol for a period of about 20 hours.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A process comprising:
   receiving a process stream including at least about 80.0% by weight propylene glycol;
   contacting the process stream with an absorbent material to produce a product stream, the absorbent material configured to preferentially absorb ethylene glycol relative to propylene glycol; and
   regenerating the absorbent material with an inert gas.

2. The process of claim 1, further comprising distilling a stream to produce the process stream.

3. The process of claim 1, further comprising conditioning the process stream to a temperature in a range of about 50° C. to about 300° C.

4. The process of claim 3, wherein the temperature is in a range of about 130° C. to about 170° C.

5. The process of claim 1, wherein the absorbent material is contained in a fixed bed system.

6. The process of claim 1, wherein regeneration of the absorbent material is carried out at a regeneration temperature of about 150° C. to about 800° C.

7. The process of claim 1, wherein the absorbent material is selected from the group consisting of a zeolite, a clay, and any combination thereof.

8. The process of claim 7, wherein the absorbent material includes a zeolite.

9. The process of claim 8, wherein the zeolite includes 4 A zeolite.

10. The process of claim 1, wherein the process stream includes ethylene glycol in an amount not greater than about 5% by weight.

11. The process of claim 10, wherein the process stream includes ethylene glycol in an amount not greater than about 2000 ppm.

12. The process of claim 11, wherein the product stream includes not greater than about 100 ppm ethylene glycol.

13. The process of claim 12, wherein the product stream includes not greater than 50 ppm ethylene glycol.

14. The process of claim 13, wherein the product stream includes not greater than about 25 ppm ethylene glycol.

15. A process for producing high purity propylene glycol, the process comprising:
   receiving a process stream including at least about 80.0% by weight propylene glycol and including ethylene glycol in an amount of less than about 5.0% by weight;
   contacting the process stream with an absorbent material to produce a product stream, the absorbent material configured to preferentially absorb the ethylene glycol; and
   regenerating the absorbent material at a regeneration temperature of about 150° C. to about 800° C.

16. The process of claim 15, wherein the absorbent material is selected from the group consisting of a zeolite, a clay, and any combination thereof.

17. The process of claim 15 wherein the absorbent material includes 4 A zeolite.

18. The process of claim 17, wherein the product stream includes not greater than about 100 ppm ethylene glycol.

19. The process of claim 18, wherein the product stream includes not greater than 50 ppm ethylene glycol.

20. The process of claim 19, wherein the product stream includes not greater than about 25 ppm ethylene glycol.

21. A process for producing high purity propylene glycol, the process comprising:
   receiving a stream including at least about 60% by weight propylene glycol and including ethylene glycol;
   distilling the stream to produce a process stream including at least about 80% by weight propylene glycol and not greater than 5% by weight ethylene glycol;
   contacting the process stream with an adsorbent material configured to preferentially absorb the ethylene glycol; and
   regenerating the absorbent material with an inert gas at a regeneration temperature of about 150° C. to about 800° C. for a period of time within a range of between about 0.5 hours to about 24 hours.

22. The process of claim 1, wherein the inert gas is selected from the group consisting of air, oxygen, nitrogen, and combinations thereof.

* * * * *